(12) United States Patent
Main et al.

(10) Patent No.: US 8,192,364 B2
(45) Date of Patent: Jun. 5, 2012

(54) METHOD FOR ASSESSING VASCULAR DISEASE BY QUANTITATIVELY MEASURING VASO VASORUM

(75) Inventors: Joan C Main, Scottsdale, AZ (US); Bijoy K Khandheria, Fountain Hills, AZ (US); A Jamil Tajik, Fountain Hills, AZ (US); Robert T Hurst, Scottsdale, AZ (US); Steven J Lester, Scottsdale, AZ (US); Christopher B Kendall, Phoenix, AZ (US); Susan Wilansky, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 92 days.

(21) Appl. No.: 12/813,476

(22) Filed: Jun. 10, 2010

(65) Prior Publication Data

US 2011/0082374 A1  Apr. 7, 2011

Related U.S. Application Data

(60) Provisional application No. 61/185,802, filed on Jun. 10, 2009.

(51) Int. Cl.
*A61B 8/14* (2006.01)
(52) U.S. Cl. .................. 600/458; 600/437; 600/462
(58) Field of Classification Search ........... 600/437–468
See application file for complete search history.

(56) References Cited

U.S. PATENT DOCUMENTS

| | | | |
|---|---|---|---|
| 6,312,383 B1* | 11/2001 | Lizzi et al. | 600/437 |
| 6,315,730 B1* | 11/2001 | Hoff et al. | 600/458 |
| 6,419,632 B1* | 7/2002 | Shiki et al. | 600/443 |
| 6,423,007 B2* | 7/2002 | Lizzi et al. | 600/458 |
| 6,540,684 B2* | 4/2003 | Averkiou et al. | 600/458 |
| 6,547,738 B2* | 4/2003 | Lysyansky | 600/458 |
| 6,612,989 B1* | 9/2003 | Brock-Fisher | 600/447 |
| 6,659,953 B1* | 12/2003 | Sumanaweera et al. | 600/443 |
| 6,689,065 B2* | 2/2004 | Aksnes et al. | 600/458 |
| 6,802,813 B2* | 10/2004 | Schutt | 600/454 |
| 7,081,092 B2* | 7/2006 | Schutt | 600/458 |
| 2001/0021371 A1* | 9/2001 | Eriksen et al. | 424/9.52 |
| 2002/0040189 A1* | 4/2002 | Averkiou et al. | 600/458 |
| 2003/0211036 A1* | 11/2003 | Degani et al. | 424/1.11 |
| 2003/0220563 A1* | 11/2003 | Schutt | 600/431 |
| 2004/0052728 A1* | 3/2004 | Eriksen et al. | 424/1.11 |
| 2004/0081623 A1* | 4/2004 | Eriksen et al. | 424/9.52 |

(Continued)

OTHER PUBLICATIONS

Redwood et al, Using ChromaFlo Intra-Vascular Ultrasound (IVUS) to Analyze Adventitial Vasa Vasorum Distribution: Consideration and Recommenations; Medical Imaging 2006: Proc. of SPIE vol. 6143; 7 pages.

(Continued)

*Primary Examiner* — Sanjay Cattungal
(74) *Attorney, Agent, or Firm* — Quarles & Brady LLP (57) ABSTRACT

A method and system for quantifying the extent of vaso vasorum with contrast enhanced ultrasound and correlating that quantitative value to the risk for vascular disease is provided. An ultrasound contrast agent is administered to a subject and images are obtained using an imaging method that identifies the uptake of the contrast agent by tissues. The amount of uptake is measured and the corresponding signal intensity change correlated with the amount of vaso vasorum present. Additionally, deformations of the vasculature are measured from the series of ultrasound images and this information is coupled with the quantification of the vaso vasorum to determine a risk index indicative of a subject's risk to vascular disease.

20 Claims, 4 Drawing Sheets

U.S. PATENT DOCUMENTS

| | | | |
|---|---|---|---|
| 2004/0230122 A1* | 11/2004 | Eriksen et al. | 600/458 |
| 2005/0049484 A1* | 3/2005 | Schutt | 600/420 |
| 2005/0234340 A1* | 10/2005 | Brock-Fisher et al. | 600/458 |
| 2006/0161062 A1* | 7/2006 | Arditi et al. | 600/443 |
| 2007/0167797 A1* | 7/2007 | Averkiou et al. | 600/458 |

OTHER PUBLICATIONS

Stieger et al, Imaging of angiogenesis using Cadence contrast pulse sequencing and targeted contrast agents, Contrast Media Mol. Imaging 2008, 3 9-18.

Molinari et al, Accurate and Automatic Carotid Plaque Characterization in Contrast Enhanced 2-D Ultrasound Images, Proc of the 29th Annual Int'l Conference of the IEEE EMBS, Aug. 23-26, 2007; pp. 335-338.

Holden et al, Value of a contrast agent in equivocal carotid ultrasound studies: Pictorial essay; Australasian Radiology (2000) 44, 253-260.

Kriegshauser et al; Carotid Pseudostring Sign From Vasa Vasorum Collaterals; J Ultraound Med 22:959-963, 2003.

Feinstein, Contrast Ultrasound Imaging of the Carotid Artery Vasa Vasorum and Atherosclerotic Plaque Neovascularization; Journal of the American College of Cardiology; vol. 28, No. 2, 2006.

Shah et al, Contrast-enhanced ultrasound imaging of atherosclerotic carotid plaque neovascularization: a new surrogate marker of atherosclerosis?, Vascular Medicine 2007; 12: 291-291.

Vicenzini et al, Detection of Carotid Adventitial Vasa Vasorum and Plaque Vascularization with Ultrasound Cadence Contrast Pulse Sequencing Technique and Echo-Contrast Agent, Stroke, Journal of the American Heart Association, Oct. 2007, pp. 2840-2843.

Paul et al, Cadence Contrast Agent Imaging Technology* on the ACUSON Sequoia Ultrasound Platform, Siemens Medical USA, Inc. 2005, 8 pages.

Jackson et al, Syngo Velocity Vector Imaging, Siemens Medical USA, Inc. 2006, 10 pages.

Vavuranakis et al, A new method for assessment of plaque vulnerability based on vasa vasorum imaging, by using contrast-enhanced intravascular ultrasound and differential image analysis, International Journal of Cardiology 130 (2008) 23-29.

* cited by examiner

METHOD FOR ASSESSING VASCULAR DISEASE BY QUANTITATIVELY MEASURING VASO VASORUM

CROSS-REFERENCE TO RELATED APPLICATIONS

This application claims the benefit of U.S. Provisional Patent Application Ser. No. 61/185,802, filed on Jun. 10, 2009, and entitled "Method for Assessing Vascular Disease by Quantitatively Measuring Vaso Vasorum."

BACKGROUND OF THE INVENTION

The field of the invention is ultrasound imaging methods and systems. More particularly, the invention relates to employing ultrasound to assess cardiac disease by quantitatively measuring vaso vasorum.

There are a number of modes in which ultrasound can be used to produce images of objects. The ultrasound transmitter may be placed on one side of the object and the sound transmitted through the object to the ultrasound receiver placed on the other side ("transmission" mode). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight", or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter", or "echo" mode).

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and their amplitude is used to modulate the brightness of pixels on a display. The location of the transducer and the time delay of the received echo signals locates the pixels to be illuminated. With the B-scan method, enough data are acquired from which a two-dimensional image of the refractors can be reconstructed. Rather than physically moving the transducer over the subject to perform a scan it is more common to employ an array of transducer elements and electronically move an ultrasonic beam over a region in the subject.

Ultrasonic transducers for medical applications are constructed from one or more piezoelectric elements sandwiched between a pair of electrodes. Such piezoelectric elements are typically constructed of lead zirconate titanate ("PZT"), polyvinylidene diflouride ("PVDF"), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere.

When used for ultrasound imaging, the transducer typically has a number of piezoelectric elements arranged in an array and driven with separate voltages ("apodizing"). By controlling the time delay (or phase) and amplitude of the applied voltages, the ultrasonic waves produced by the piezoelectric elements ("transmission mode") combine to produce a net ultrasonic wave focused at a selected point. By controlling the time delay and amplitude of the applied voltages, this focal point can be moved in a plane to scan the subject.

The same principles apply when the transducer is employed to receive the reflected sound ("receiver mode"). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the echo signal received by each transducer array element.

Doppler systems employ an ultrasonic beam to measure the velocity of moving reflectors, such as flowing blood cells. Blood velocity is detected by measuring the Doppler shifts in frequency imparted to ultrasound by reflection from moving red blood cells. Accuracy in detecting the Doppler shift at a particular point in the bloodstream depends on defining a small sample volume at the required location and then processing the echoes to extract the Doppler shifted frequencies.

A Doppler system is incorporated in a real time scanning imaging system. The system provides electronic steering and focusing of a single acoustic beam and enables small volumes to be illuminated anywhere in the field of view of the instrument, whose locations can be visually identified on a two-dimensional B-scan image. A Fourier transform processor faithfully computes the Doppler spectrum backscattered from the sampled volumes, and by averaging the spectral components the mean frequency shift can be obtained. Typically the calculated blood velocity is used to color code pixels in the B-scan image.

In areas of injured endothelial lining, tiny blood vessels referred to as vaso vasorum are formed to supply these areas. These inflamed areas are vulnerable to form plaque. It would therefore be desirable to have a method for not only visualizing the presence of vaso vasorum, but to quantify their presence and effect.

SUMMARY OF THE INVENTION

The present invention is directed to a method for measuring the risk a tissue of interest has for developing vascular disease. More particularly, the present invention is a method for quantifying the extent of vaso vasorum with contrast enhanced ultrasound and correlating that quantitative value to the risk for vascular disease. An ultrasound contrast agent is administered to a subject and images are obtained using an imaging method that identifies the uptake of the contrast agent by tissues. The amount of uptake is measured and the corresponding signal intensity change correlated with the amount of vaso vasorum present. Additionally, deformations of the vasculature are measured from the series of ultrasound images and this information is coupled with the quantification of the vaso vasorum to determine a risk index indicative of a subject's risk to vascular disease.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
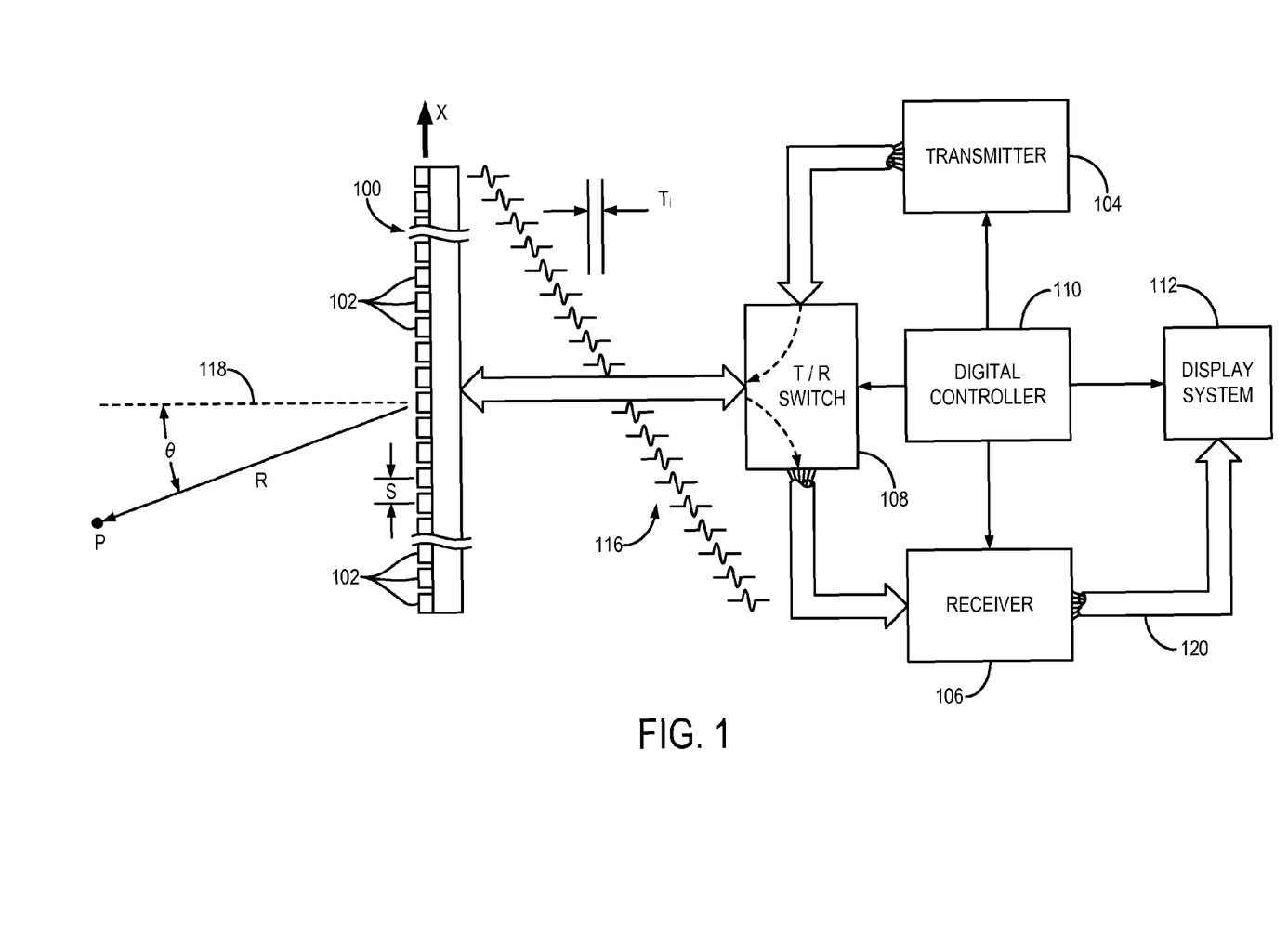
FIG. 1 is a block diagram of an ultrasonic imaging system that employs the present invention.

Referring particularly to FIG. 1, an ultrasonic imaging system includes a transducer array 100 comprised of a plurality of separately driven elements 102 which each produce a burst of ultrasonic energy when energized by a pulse produced by a transmitter 104. The ultrasonic energy reflected back to the transducer array 100 from the subject under study is converted to an electrical signal by each transducer element 102 and applied separately to a receiver 106 through a set of switches 108. The transmitter 104, receiver 106, and the switches 108 are operated under the control of a digital controller 110 responsive to the commands input by the human operator. A complete scan is performed by acquiring a series of echoes in which the switches 108 are set to their transmit position, the transmitter 104 is gated on momentarily to energize each transducer element 102, the switches 108 are then set to their receive position, and the subsequent echo signals produced by each transducer element 102 are applied to the receiver 106. The separate echo signals from each transducer element 102 are combined in the receiver 106 to produce a single echo signal which is employed to produce a line in an image on a display system 112.

The transmitter 104 drives the transducer array 100 such that the ultrasonic energy produced is directed, or steered, in a beam. A B-scan can therefore be performed by moving this beam through a set of angles from point-to-point rather than physically moving the transducer array 100. To accomplish this the transmitter 104 imparts a time delay, T, to the respective pulses 116 that are applied to successive transducer elements 102. If the time delay is zero $T_i=0$, all the transducer elements 102 are energized simultaneously and the resulting ultrasonic beam is directed along an axis 118 normal to the transducer face and originating from the center of the transducer array 100. As the time delay, $T_i$, is increased, the ultrasonic beam is directed downward from the central axis 118 by an angle, θ. The relationship between the time delay increment, $T_i$, added successively to each $i^{th}$ signal from one end of the transducer array (i=1) to the other end (i=n) is given by the following relationship:

$$T_i = \left(i - \frac{(n-1)}{2}\right)\left(\frac{S\sin(\theta)}{c}\right) + \left(i - \frac{(n-1)}{2}\right)^2\left(\frac{S^2\cos(2\theta)}{2Rc}\right) + T_0; \quad \text{Eqn. (1)}$$

where S is an equal spacing between centers of adjacent transducer elements 102, c is the velocity of sound in the object under study, R is a range at which the transmit beam is to be focused, and $T_0$ is a delay offset that insures that all calculated values, $T_i$, are positive values.

The first term in this expression steers the beam in the desired angle, θ, and the second is employed when the transmitted beam is to be focused at a fixed range. A sector scan is performed by progressively changing the time delays, $T_i$, in successive excitations. The angle, θ, is thus changed in increments to steer the transmitted beam in a succession of directions. When the direction of the beam is above the central axis 118, the timing of the pulses 116 is reversed, but the above formula still applies.

Referring still to FIG. 1, the echo signals produced by each burst of ultrasonic energy emanate from reflecting objects located at successive positions, R, along the ultrasonic beam. These are sensed separately by each segment 102 of the transducer array 100 and a sample of the magnitude of the echo signal at a particular point in time represents the amount of reflection occurring at a specific range, R. Due to the differences in the propagation paths between a focal point, P, and each transducer element 102, however, these echo signals will not occur simultaneously and their amplitudes will not be equal. The function of the receiver 106 is to amplify and demodulate these separate echo signals, impart the proper time delay to each and sum them together to provide a single echo signal which accurately indicates the total ultrasonic energy reflected from each focal point, P, located at successive ranges, R, along the ultrasonic beam oriented at the angle, θ.

Under the direction of the digital controller 110, the receiver 106 provides delays during the scan such that the steering of the receiver 106 tracks with the direction of the beam steered by the transmitter 104 and it samples the echo signals at a succession of ranges and provides the proper delays to dynamically focus at points, P, along the beam. Thus, each emission of an ultrasonic pulse results in the acquisition of a series of data points which represent the amount of reflected sound from a corresponding series of points, P, located along the ultrasonic beam.

Figure 2:
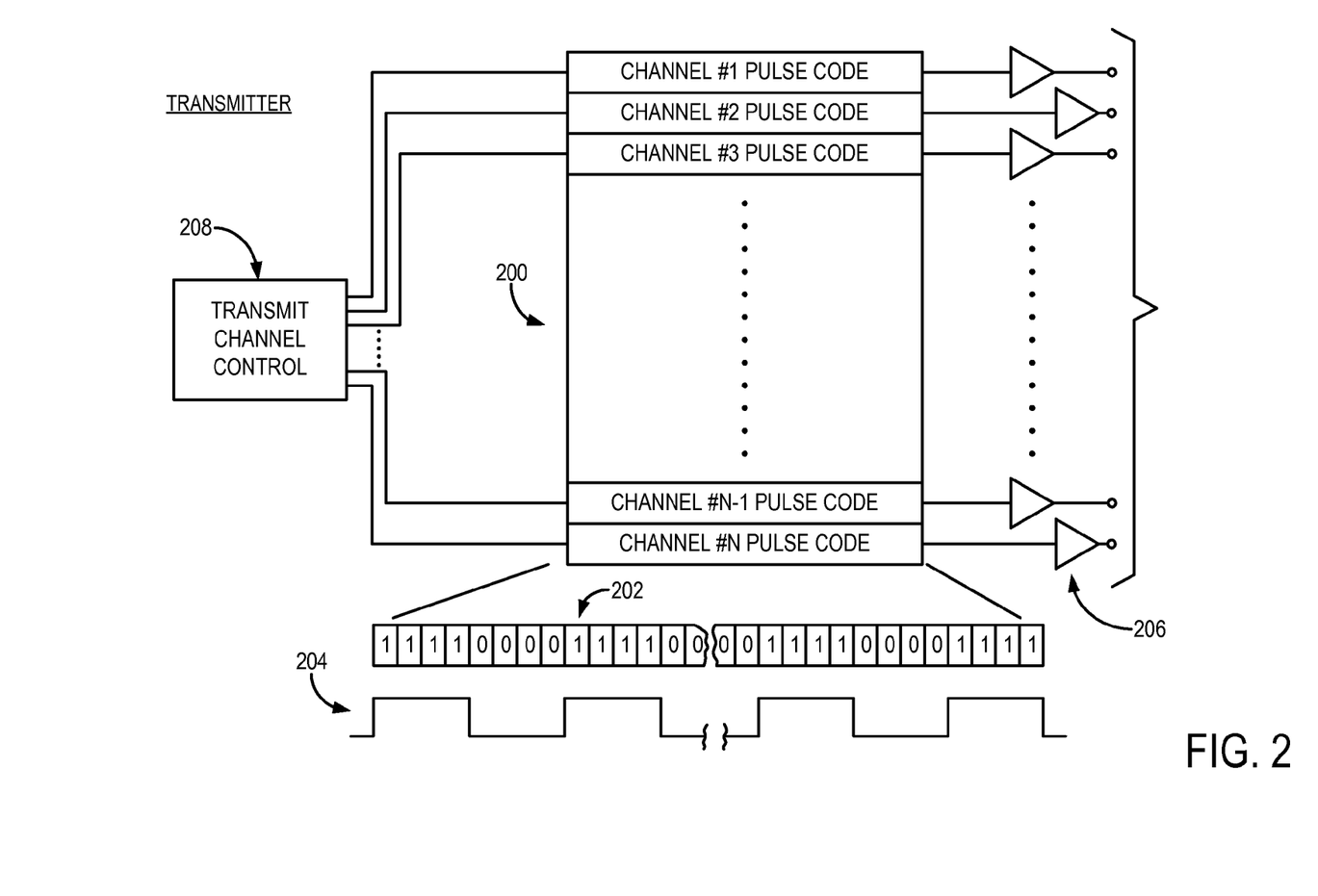
FIG. 2 is a block diagram of a transmitter which forms part of the ultrasonic imaging system of FIG. 1.

Referring particularly to FIG. 2, the transmitter 104 includes a set of channel pulse code memories which are indicated collectively at 200. Each pulse code memory 200 stores a bit pattern 202 that determines the frequency of the ultrasonic pulse 204 that is to be produced. This bit pattern is read out of each pulse code memory 200 by a master clock and applied to a driver 206 which amplifies the signal to a power level suitable for driving the transducer 100. In the example shown in FIG. 2, the bit pattern is a sequence of four "1" bits alternated with four "0" bits to produce a 5 megahertz ("MHz") ultrasonic pulse 204. The transducer elements 102 to which these ultrasonic pulses 204 are applied respond by producing ultrasonic energy.

As indicated above, to steer the transmitted beam of the ultrasonic energy in the desired manner, the pulses 204 for each of the N channels must be produced and delayed by the proper amount. These delays are provided by a transmit control 208 which receives control signals from the digital controller 110. When the control signal is received, the transmit control 208 gates a clock signal through to the first transmit channel 200. At each successive delay time interval thereafter, the clock signal is gated through to the next channel pulse code memory 200 until all the channels to be energized are producing their ultrasonic pulses 204. Each transmit channel 200 is reset after its entire bit pattern 202 has been transmitted and the transmitter 104 then waits for the next control signal from the digital controller 110. By operating the transmitter 104 in this manner, ultrasonic energy can be focused on a focal point, P, when practicing the herein described method. This focal point can be steered electronically with the appropriate changes to the timing delays provided by the transmit control 208. The term "focal point," as referred to herein, includes not only a single point object in the usual sense, but also a general region-of-interest to which ultrasound energy is delivered in a substantially focused manner.

Figure 3:
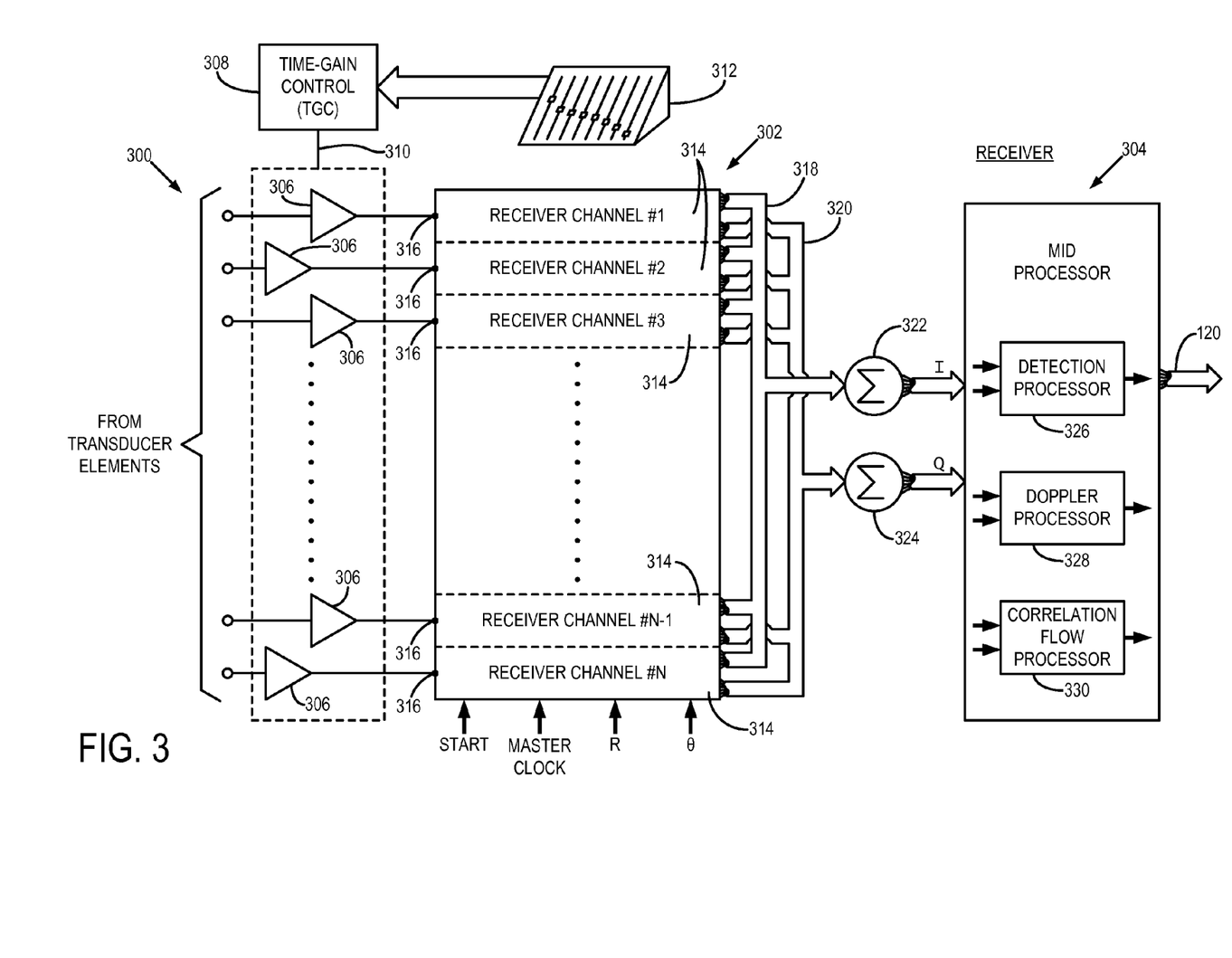
FIG. 3 is a block diagram of a receiver which forms part of the ultrasonic imaging system of FIG. 1.

Referring particularly to FIG. 3, the receiver 106 is comprised of three sections: a time-gain control ("TGC") section 300, a beam forming section 302, and a mid processor 304. The time-gain control section 300 includes an amplifier 306 for each of the N receiver channels and a time-gain control circuit 308. The input of each amplifier 306 is connected to a respective one of the transducer elements 102 to receive and amplify the echo signal which it receives. The amount of amplification provided by the amplifiers 306 is controlled through a control line 310 that is driven by the time-gain control circuit 308. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by the operator who manually sets TGC linear potentiometers 312 to values which provide a relatively uniform brightness over the entire range of the scan. The time interval over which the echo signal is acquired determines the range from which it emanates, and this time interval is divided into segments by the TGC control circuit 308. The settings of the potentiometers are employed to set the gain of the amplifiers 306 during each of the respective time intervals so that the echo signal is amplified in ever increasing amounts over the acquisition time interval.

The beam forming section 302 of the receiver 106 includes N separate receiver channels 314. Each receiver channel 314 receives the analog echo signal from one of the TGC amplifiers 306 at an input 316, and it produces a stream of digitized output values on an I bus 318 and a Q bus 320. Each of these I and Q values represents a sample of the echo signal envelope at a specific range, R. These samples have been delayed in the manner described above such that when they are summed at summing points 322 and 324 with the I and Q samples from each of the other receiver channels 314, they indicate the magnitude and phase of the echo signal reflected from a point, P, located at range, R, on the ultrasonic beam.

Referring still to FIG. 3, the mid processor section 304 receives the beam samples from the summing points 322 and 324. The I and Q values of each beam sample is a digital number which represents the in-phase and quadrature components of the magnitude of the reflected sound from a point, P. The mid processor 304 can perform a variety of calculations on these beam samples, where choice is determined by the type of image to be reconstructed. For example, if a conventional magnitude image is to be produced, a detection processor indicated at 326 is implemented in which a digital magnitude, M, is calculated from each beam sample according to:

$$M = \sqrt{I^2 + Q^2}$$ Eqn. (2);

and output at 120 (FIGS. 1 and 3).

The detection processor 326 may also implement correction methods that, for example, examine the received beam samples and calculate corrective values that can be used in subsequent measurements by the transmitter 104 and receiver 106 to improve beam focusing and steering. Such corrections are necessary, for example, to account for the non-homogeneity of the media through which the sound from each transducer element travels during a scan.

The mid processor may also include a Doppler processor 328. Such Doppler processors 328 often employ the phase information, $\phi$, contained in each beam sample to determine the velocity of reflecting objects along the direction of the beam (i.e., direction from the transducer 100), where:

$$\varphi = \tan^{-1}\left(\frac{I}{Q}\right).$$ Eqn. (3)

The mid processor 304 may also include a correlation flow processor 330 that, for example, measures the motion of reflectors by following the shift in their position between successive ultrasonic pulse measurements.

Figure 4:
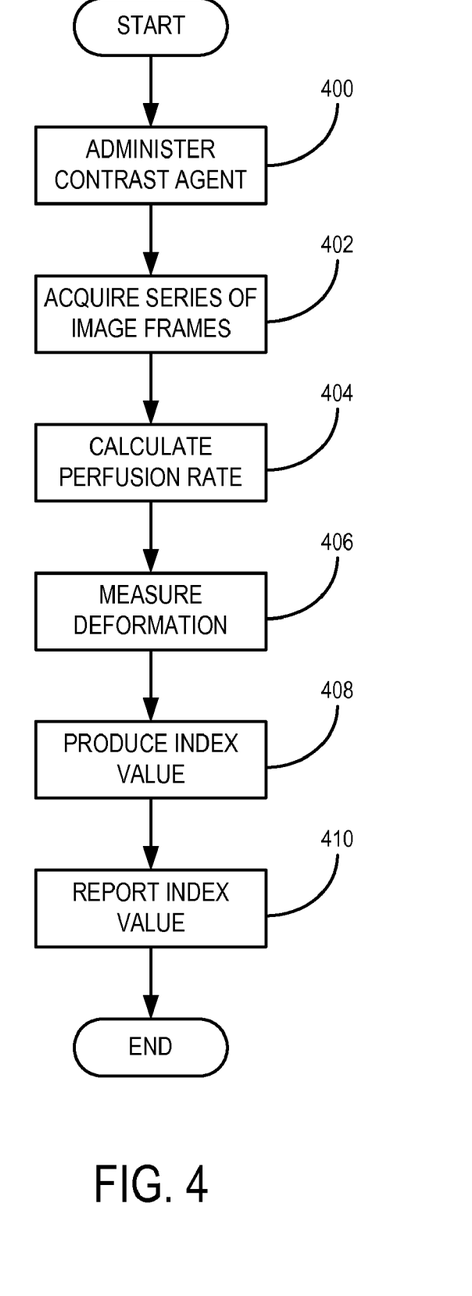
FIG. 4 is a flowchart setting forth the steps of an embodiment of the present invention.

Referring particularly now to FIG. 4, a method for quantitatively measuring vaso vasorum, and thereby assessing vascular disease, in accordance with the present invention begins with the administration of an ultrasound contrast agent to a subject, as indicated at step 400. Exemplary ultrasound contrast agents include those with the trade names SonoVue® (Bracco Diagnostics, Princeton, N.J.), Definity® (Lantheus Medical Imaging, North Billerica, Mass.), Optison (GE Healthcare, Waukesha, Wis.), and Imagent® (IMCOR Pharmaceutical Co., San Diego, Calif.). After the contrast agent has been administered to the subject, a series of image frames are acquired, as indicated at step 402. The images acquired discriminate between the contrast agent and the background tissues. For example, a contrast pulse sequencing method is employed in which background tissue is separable from the contrast agent by way of simultaneously processing received signals from a plurality of transmitted pulses. The phase and amplitude modulation of each pulse is varied so that the interaction of the pulses with the contrast agent results in a response that is separable from background tissues. An exemplary imaging method of this kind is available under the trade name Cadence™ contrast pulse sequencing (Siemens Medical Solutions USA, Inc., Mountain View, Calif.).

From the acquired series of image frames, a perfusion rate of the contrast agent into the surrounding vasculature is determined at step 404. The rate of perfusion of the contrast agent into the surrounding tissues provides a quantitative measure of the presence of vaso vasorum in the vessel. Where an increase in the perfusion of the contrast agent into the vascular wall occurs, an increase in signal intensity is present in the resulting images. The degree of perfusion of the contrast agent into the vascular wall is representative of the presence of vaso vasorum. To calculate the perfusion rate, the change in image intensity over the series of acquired images is analyzed. The signal intensity change in a selected region of interest is fit on a voxel-by-voxel basis to the following signal model:

$$A + B(1 - e^{-kt})$$ Eqn. (4);

where A is constant indicative of the peak image intensity of contrast agent uptake, B is a constant indicative of the perfusion rate, k is a constant, and t is the time at which a given image frame was acquired. The constant B is calculated from the logarithm of the measured signal intensity change. It is contemplated that values of the constant, B, greater than 0.50 indicate the presence of vaso vasorum in the blood vessel of interest. It is also contemplated that the peak image intensity value, A, can be utilized to determine the presence of vaso vasorum, in as much as larger peak values are likely representative of the presence of more vaso vasorum in the vessel wall, which in turn provide a larger uptake of the contrast agent.

The acquired series of image frames are then also analyzed using a tracking technique that measures deformations in the vessel wall, as indicated at step 406. An exemplary method of this kind is available under the trade name Velocity Vector Imaging™ (Siemens Medical Solutions USA, Inc., Mountain View, Calif.). Using a motion tracking method, such as the one provided by Velocity Vector Imaging™, radial deformations and rotations in a vessel wall are determined. Additionally, longitudinal and cross-sectional blood flow velocities through the blood vessel of interest can be calculated and utilized to assess the risk for vascular disease. This information, along with the perfusion rate calculated previously, is utilized to produce an index value, as indicated at step 408. The index value indicates those tissues of interest that are at risk for a particular vascular disease.

After the index value has been produced, it is reported to the system operator, ultrasound technologist, clinician, or other healthcare professional, as indicated at step 410. For example, an index map is produced, in which voxel values in the index map correspond to the index value calculated for the corresponding voxel location in the acquired series of image frames. An exemplary index map includes a discontinuous color coding scheme that indicates those regions where vaso vasorum are present and the degree of vulnerability for those regions to develop vascular disease. For example, an index value in the 75-100 percentile range is coded as red, 50-75 percentile range is coded as orange, 25-50 percentile range is coded as yellow, and 0-25 percentile range is coded as blue. By way of this example, those regions coded as red indicate areas at very high risk for vascular disease, while those coded as orange are at high risk, those coded as yellow are areas at moderate risk, and those coded as blue are at low risk. Alternatively, when the index values include values in the range identified as "risk", a report can be produced indicating that the subject is at risk for particular a vascular disease.

Additionally, the quantified presence of vaso vasorum provided by the calculated perfusion rate in the lumen of the blood vessel can be utilized alone to assess the risk of the patient to developing vascular disease. For example, different threshold values of perfusion rate can be used to identify different risk groups. By way of example, the following ranges of values for the constant, B, can be used: 0-0.50, low risk; 0.50-5.0, higher risk; and greater than 5.0, even higher risk. Furthermore, this risk assessment can be supplemented with information regarding the deformation of the blood vessel wall. For instance, it is contemplated that the more cross-sectional rotational or radial deformation present in the vessel wall, the more likely the patient is at risk for developing vascular disease. The peak uptake of the contrast agent into the lumen of the blood vessel can also be utilized to assess the risk of the patient. For example, it is contemplated that a patient having a large uptake in contrast agent is more likely to have vaso vasorum present than a patient with less uptake.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an index indicative of vascular disease in a subject with an ultrasound imaging system, the steps comprising:
    a) administering a contrast agent to the subject;
    b) acquiring, with the ultrasound imaging system, a series of image frames from the subject during a passage of the contrast agent through a tissue of interest in the subject;
    c) calculating, from the series of image frames, a perfusion rate in the tissue of interest;
    d) calculating, from the series of image frames, information indicative of a deformation of the tissue of interest; and
    e) producing an index indicative of vascular disease using the calculated perfusion rate and calculated information indicative of the deformation of the tissue of interest.

2. The method as recited in claim 1 in which step c) includes analyzing changes in image intensity in the series of image frames as the contrast agent passes through the tissue of interest.

3. The method as recited in claim 2 in which step c) further includes:
    i) calculating a logarithm of the image intensity in each of the image frames in the series;
    ii) producing a fit of the calculated logarithms; and
    iii) determining a slope of the fit, the slope of the fit being proportional to the perfusion rate in the tissue of interest.

4. The method as recited in claim 1 in which the information indicative of deformation of the tissue of interest includes at least one of rotation and radial deformation of the tissue of interest.

5. The method as recited in claim 1 further including:
    f) producing an image indicative of vascular disease using the index produced in step e).

6. The method as recited in claim 5 in which step f) includes assigning pixel values in the image using the produced index.

7. The method as recited in claim 6 in which step f) further includes assigning the pixel values using a discontinuous color scheme, in which pixel locations are assigned a pixel value from a selected set of pixel values based on the produced index associated with the pixel location.

8. The method as recited in claim 7 in which the selected set of pixel values includes a very high risk pixel value, a high risk pixel value, a moderate risk pixel value, and a low risk pixel value.

9. The method as recited in claim 8 in which a pixel location is assigned the very high risk pixel value when the produced index is in around a 75-100 percentile range, the high risk pixel value when the produced index is in around a 50-75 percentile range, the moderate risk pixel value when the produced index is in around a 25-50 percentile range, and the low risk pixel value when the produced index is in around a 0-25 percentile range.

10. The method as recited in claim 8 in which the very high risk pixel value is red, the high risk pixel value is orange, a moderate risk pixel value is yellow, and a low risk pixel value is blue.

11. The method as recited in claim 1 in which the tissue of interest is a blood vessel.

12. The method as recited in claim 11 in which the perfusion rate calculated in step c) is indicative of a presence of vaso vasorum in the blood vessel.

13. An ultrasound imaging apparatus for assessing a risk of vascular disease in a subject by quantifying vaso vasorum in a blood vessel of the subject as an ultrasound contrast agent passes through the blood vessel, the ultrasound imaging apparatus comprising:
    an ultrasound transducer;
    a transmitter in communication with the ultrasound transducer and configured to provide transmission signals to the ultrasound transducer so that in response to the transmission signals the ultrasound transducer delivers ultrasound energy to the blood vessel;
    a receiver in communication with the ultrasound transducer and configured to receive echo signals indicative of ultrasound echoes produced in response to the ultrasound energy delivered to the blood vessel and detected by the ultrasound transducer; and an image processor in communication with the receiver and configured to receive the received echo signals, the image processor being further configured to:
  i) reconstruct from the received echo signals, a series of image frames depicting the blood vessel;
  ii) calculate from the series of image frames, a perfusion rate in a lumen of the blood vessel, the perfusion rate being quantitatively indicative of a presence of vaso vasorum in the blood vessel;
  iii) calculate from the series of image frames, information indicative of a deformation of the blood vessel; and
  iv) produce an index indicative of a risk of vascular disease using the calculated perfusion rate and calculated information indicative of the deformation of the blood vessel.

14. The ultrasound imaging apparatus as recited in claim 13 in which the image processor is further configured to calculate the perfusion rate by analyzing changes in image intensity in the series of image frames.

15. The ultrasound imaging apparatus as recited in claim 14 in which analyzing changes in the image intensity in the series of image frames includes calculating a logarithm of the image intensity in each of the image frames in the series; producing a fit of the calculated logarithms; and determining a slope of the fit, the slope of the fit being proportional to the perfusion rate in the lumen of the blood vessel.

16. The ultrasound imaging apparatus as recited in claim 13 in which information indicative of a deformation of the blood vessel includes at least one of a rotation and a radial deformation of the blood vessel.

17. The ultrasound imaging apparatus as recited in claim 11 in which the image processor is further configured to produce a risk map using the produced index indicative of a risk of vascular disease and the reconstructed series of image frames, the risk map depicting portions of the reconstructed series of image frames that are at different levels of risk for vascular disease.

18. The ultrasound imaging apparatus as recited in claim 17 in which the risk map depicts different levels of risk for vascular disease using a discontinuous color scheme in which red is associated with very high risk, orange is associated with high risk, yellow is associated with moderate risk, and blue is associated with low risk.

19. The ultrasound imaging apparatus as recited in claim 17 further comprising a display in communication with the image processor and configured to receive and display to a user, the reconstructed series of image frames and the produced risk map.

20. A method for quantifying a presence of vaso vasorum in a blood vessel of a patient with an ultrasound imaging system, the steps comprising:
  a) administering a contrast agent to the patient;
  b) acquiring with the ultrasound imaging system, a series of image frames from the patient during a passage of the contrast agent through a blood vessel in the subject;
  c) calculating from the series of image frames, a perfusion rate in a lumen of the blood vessel; and
  d) quantifying a presence of vaso vasorum in the blood vessel using the calculated perfusion rate.

* * * * *